United States Patent
Fabre et al.

(10) Patent No.: US 12,251,299 B2
(45) Date of Patent: Mar. 18, 2025

(54) METHOD FOR AUTOMATED PRODUCTION OF A VASCULAR ENDOPROSTHESIS

(71) Applicant: FONDATION HOPITAL SAINT-JOSEPH, Paris (FR)

(72) Inventors: Dominique Fabre, Garches (FR); Stéphan Haulon, Paris (FR)

(73) Assignee: FONDATION HÔPITAL SAINT-JOSEPH, Paris (FR)

( * ) Notice: Subject to any disclaimer, the term of this patent is extended or adjusted under 35 U.S.C. 154(b) by 798 days.

(21) Appl. No.: 17/420,443

(22) PCT Filed: Jan. 3, 2020

(86) PCT No.: PCT/EP2020/050071
§ 371 (c)(1),
(2) Date: Jul. 2, 2021

(87) PCT Pub. No.: WO2020/141211
PCT Pub. Date: Jul. 9, 2020

(65) Prior Publication Data
US 2022/0079737 A1    Mar. 17, 2022

(30) Foreign Application Priority Data
Jan. 3, 2019    (FR) ...................................... 1900042

(51) Int. Cl.
*B33Y 70/00*    (2020.01)
*A61F 2/00*    (2006.01)
(Continued)

(52) U.S. Cl.
CPC .............. *A61F 2/06* (2013.01); *A61F 2/0077* (2013.01); *B29C 64/118* (2017.08); *B33Y 50/00* (2014.12);
(Continued)

(58) Field of Classification Search
CPC ....... B29C 64/10; B29C 64/118; B29C 64/20; B29C 64/30; B33Y 50/00; B33Y 70/00;
(Continued)

(56) References Cited

U.S. PATENT DOCUMENTS 7,597,775 B2 * 10/2009 Sogard .................... B29C 48/32
156/244.11
9,107,739 B2    8/2015 Lelkes et al.
(Continued)

FOREIGN PATENT DOCUMENTS

JP    2016520382 A    7/2016
JP    2018522601 A    8/2018
(Continued)

OTHER PUBLICATIONS

French Search Report, French Application No. 1900042, dated Nov. 11, 2019.
(Continued)

*Primary Examiner* — Nahida Sultana
(74) *Attorney, Agent, or Firm* — MARSHALL, GERSTEIN & BORUN LLP

(57) ABSTRACT

The invention relates to a method for producing a vascular endoprosthesis for insertion into a natural cavity of a person's body. The method is based on a three-dimensional model including a main channel, at least one branch of the channel extending from the main channel, and an intersection between the main channel and the branch of the channel. The method includes producing an imprint structure which is designed to follow a shape of the main channel, the imprint structure comprising at least one location corresponding to the intersection of the three-dimensional model, placing a reinforcement at the location of the imprint structure, producing a wall using the imprint structure, the prosthesis wall being made of polymer, a window or a
(Continued)

branch of the prosthesis being produced at the location, producing the vascular endoprosthesis including the window or branch of the prosthesis.

13 Claims, 7 Drawing Sheets

(51) Int. Cl.
    *A61F 2/06*     (2013.01)
    *B29C 64/118*     (2017.01)
    *B33Y 10/00*     (2015.01)
    *B33Y 50/00*     (2015.01)
    *B33Y 80/00*     (2015.01)

(52) U.S. Cl.
CPC ............... *B33Y 70/00* (2014.12); *B33Y 80/00* (2014.12); *A61F 2002/065* (2013.01); *A61F 2210/0014* (2013.01); *A61F 2230/0069* (2013.01); *A61F 2240/004* (2013.01); *A61F 2250/0058* (2013.01); *B33Y 10/00* (2014.12)

(58) Field of Classification Search
CPC .. B33Y 80/00; A61F 2/0077; A61F 2002/065; A61F 2210/0014; A61F 2230/0069; A61F 2240/004; A61F 2250/0058
See application file for complete search history.

(56) References Cited

U.S. PATENT DOCUMENTS

2011/0054594 A1*   3/2011   Mayberry ............... A61F 2/856
                                                                           29/446
2018/0368968 A1   12/2018   Leeson et al.
2018/0370141 A1*   12/2018   Eller ..................... B29C 64/291

FOREIGN PATENT DOCUMENTS

WO     WO-2004/026183 A2     4/2004
WO     WO-2004/026183 A3     1/2005
WO     WO-2017158288 A1 *   9/2017   ............... A61F 2/06

OTHER PUBLICATIONS

International Search Report and Written Opinion, International Application No. PCT/EP2020/050071, dated Jan. 17, 2020.
Office Action, Korean Patent Application No. 10-2021-7024581, dated Jun. 18, 2024.

* cited by examiner

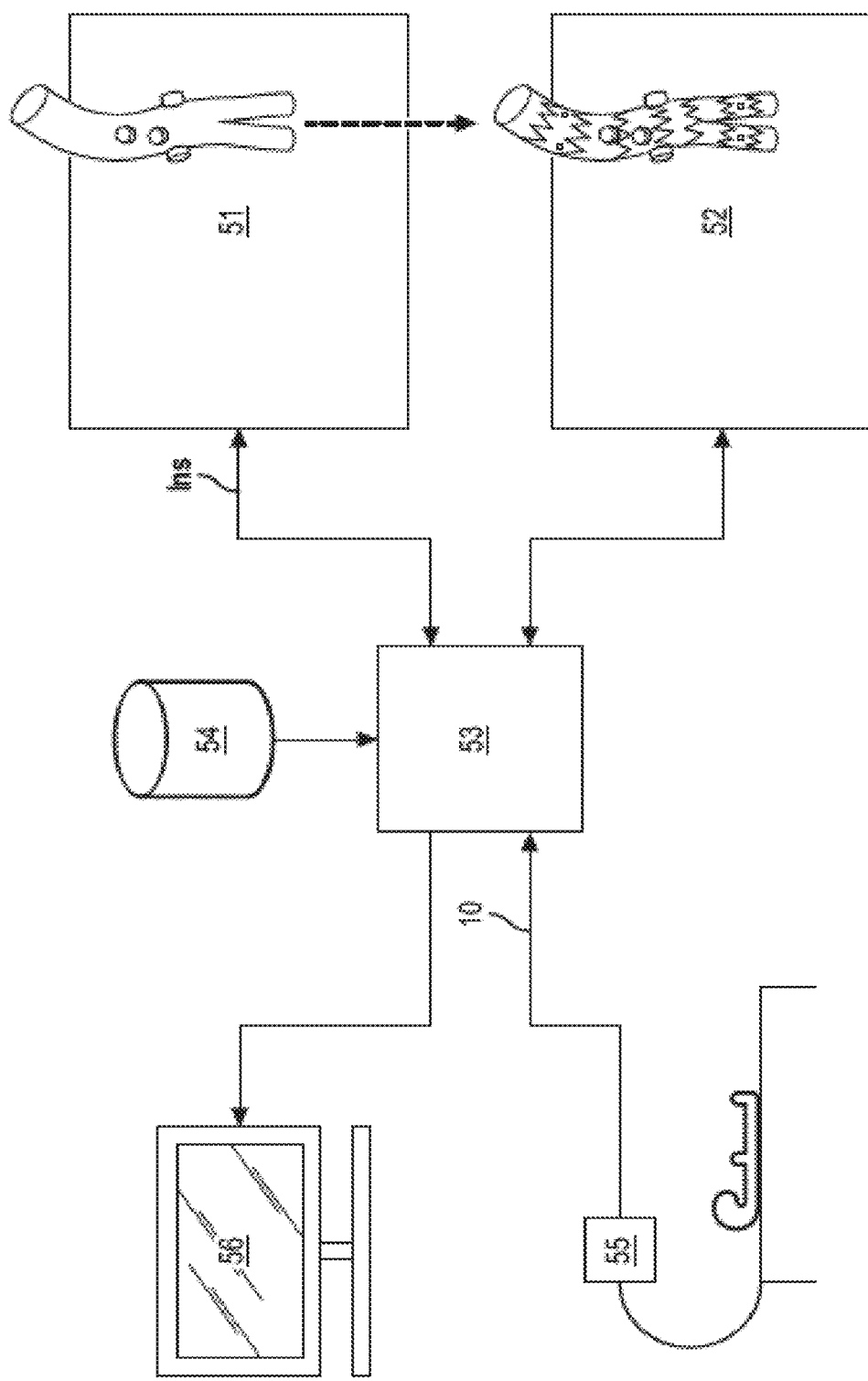
[Fig. 1]

[Fig.2]
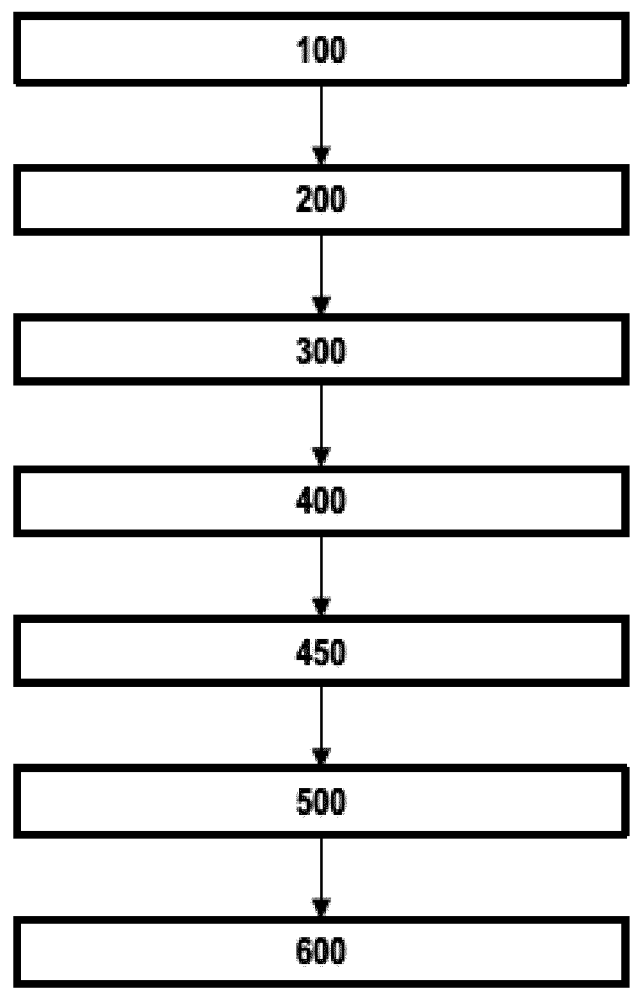

[Fig.3]
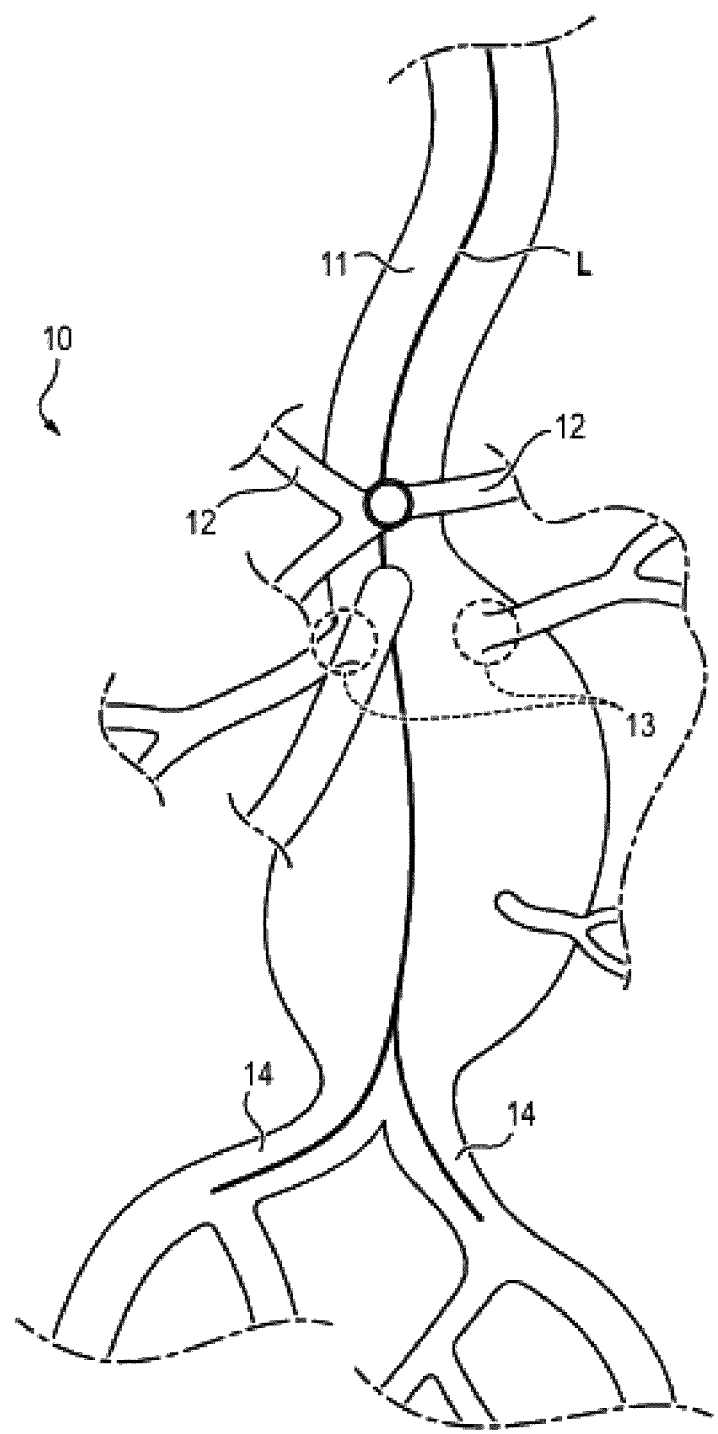

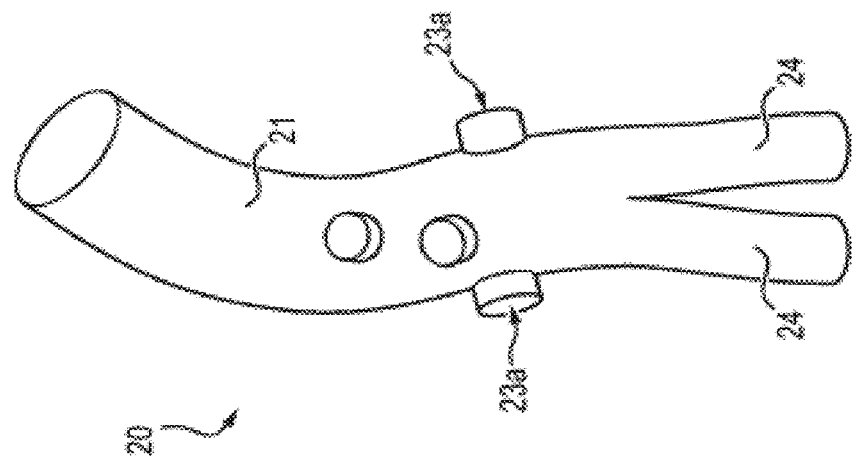
[Fig. 4]
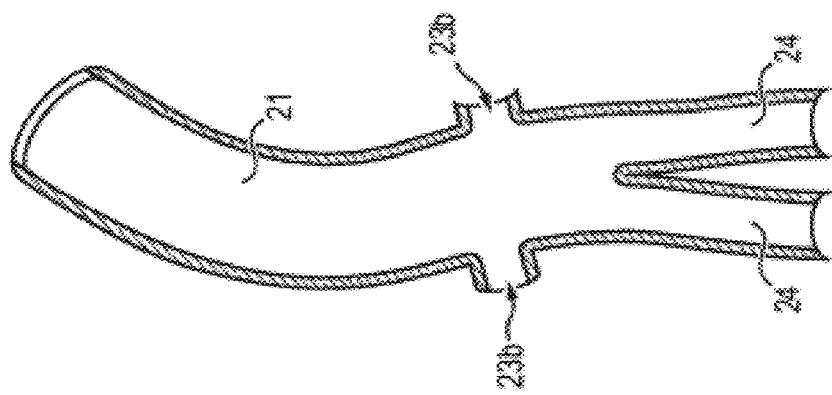
[Fig. 5]

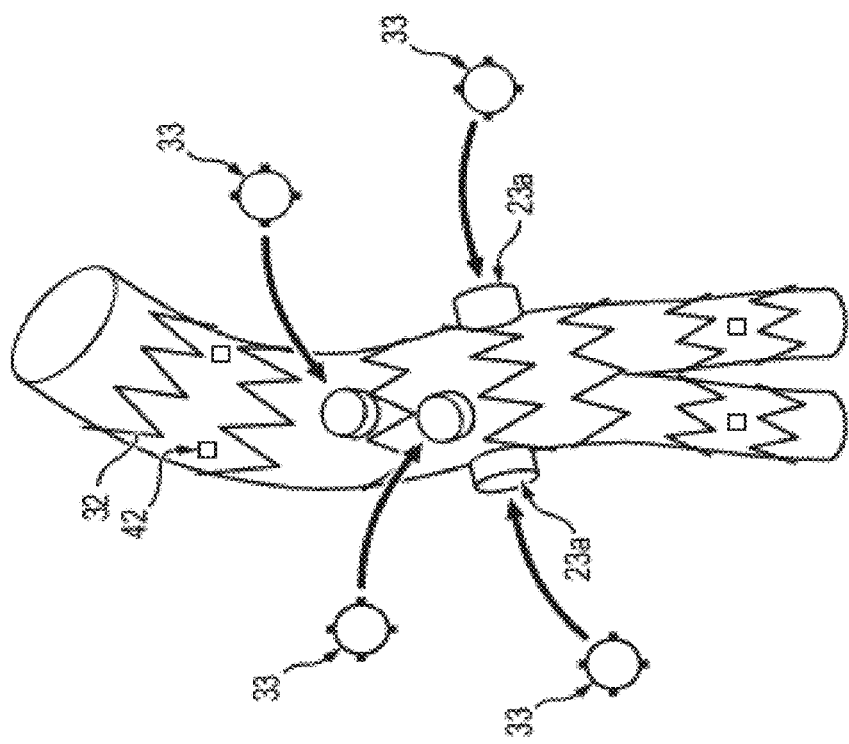
[Fig. 6]
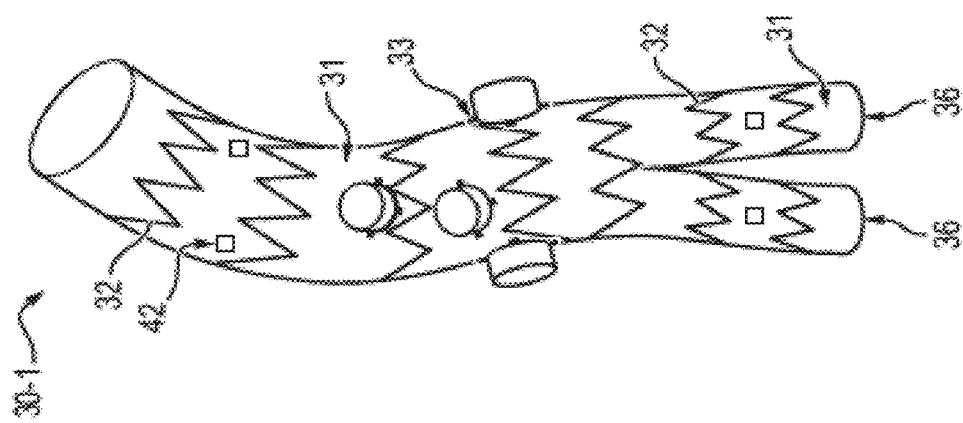
[Fig. 7]

[Fig.8]
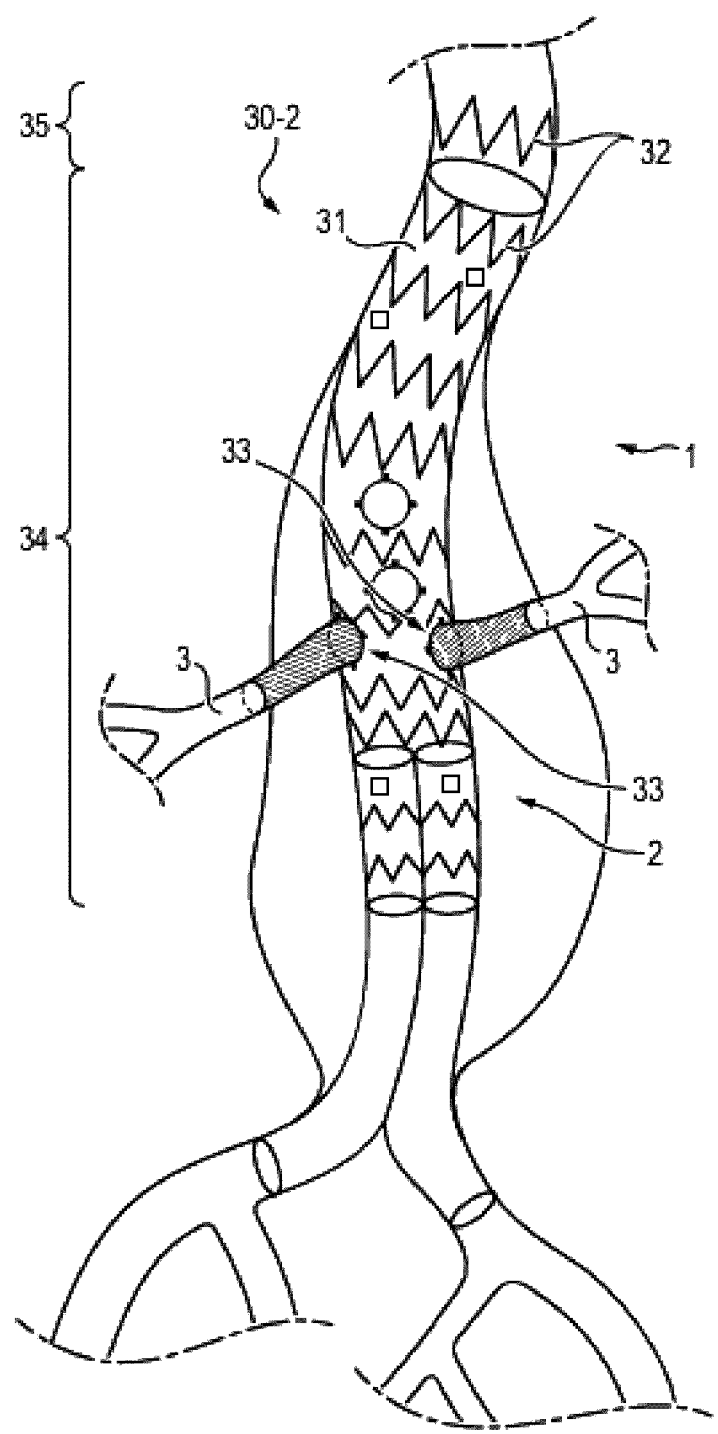

[Fig.9]
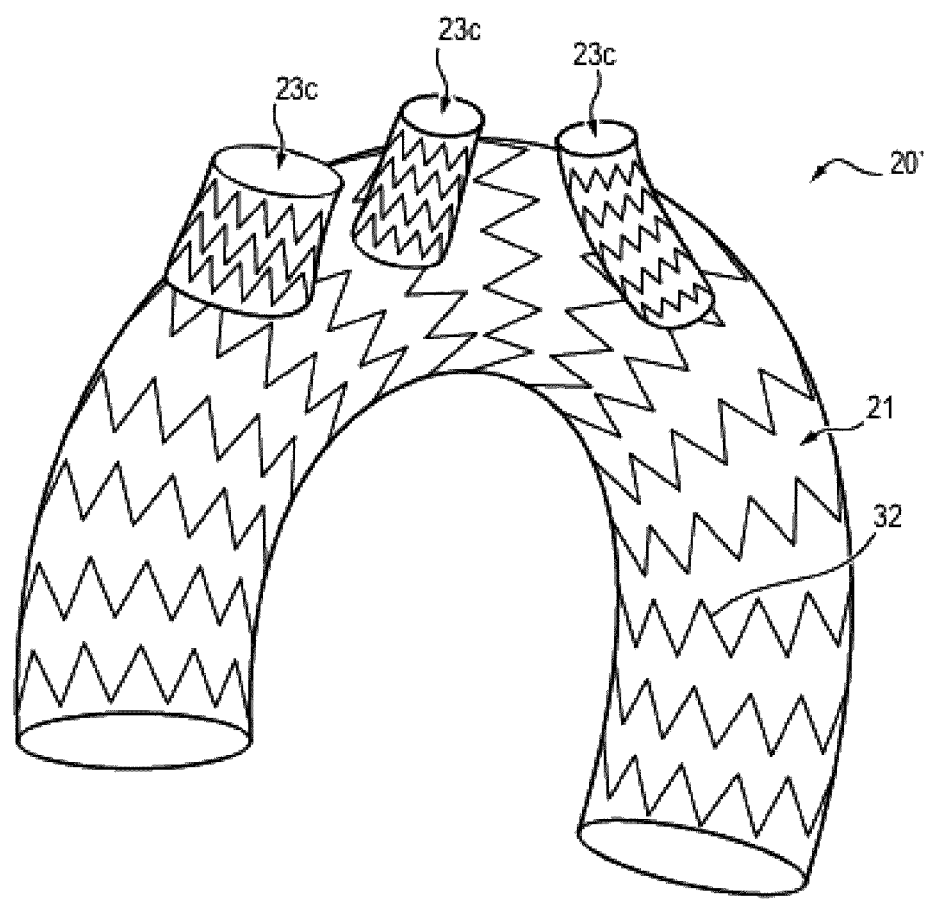

METHOD FOR AUTOMATED PRODUCTION OF A VASCULAR ENDOPROSTHESIS

CROSS-REFERENCE TO RELATED APPLICATION

This application is a U.S. national stage of International Patent Application No. PCT/EP2020/050071 filed on Jan. 3, 2020, which claims the benefit of priority of French Patent Application No. 1900042 filed on Jan. 3, 2019, the respective disclosures of which are each incorporated herein by reference in their entireties.

FIELD OF THE INVENTION

The invention relates to implantable medical devices, more precisely to bespoke medical endoprostheses used in cardiology or in vascular surgery.

It especially relates to an automated production method of a bespoke windowed and/or branched endoprosthesis, adapted to a natural cavity which can include bifurcations such as an aorta.

BACKGROUND

For production of endoprostheses, that is, prostheses designed for implantation inside the organism, a precut mesh made of biocompatible metal optionally stitched onto a polymer membrane is most frequently used.

After implantation the final prosthesis is intended to extend into a natural cavity of a patient. A natural cavity of an individual is a blood vessel, for example. The synthetic material of the prosthesis forms a wall which exhibits watertightness to biological fluids and a particular rigidity after its expansion, and forms a passage for natural fluids such as blood.

An aneurism for example can be treated by means of an endoprosthesis of tubular shape. The wall of the prosthesis must exhibit a particular rigidity and sealing zones so it can limit the risks of leaks after it is positioned.

Other arterial lesions can also be treated with this type of prosthesis.

Measuring operations, then manual production extend design and production times of vascular endoprostheses intended for complex pathologies to many weeks or even several months.

The branches of the aorta constitute bifurcations which require an endoprosthesis to be designed having "windows" or "branches" located in the region of the intersections between the main channel and the aorta branches. By default, blood circulation is blocked in the aorta branches, once the endoprosthesis is implanted in the patient. Making such a prosthesis further extends design and production times, the windows and/or branches mainly being made by cut outs and manual stitching on an existing prosthesis.

To best find out the position and the orientation of the aorta branches, it is necessary to analyse vascular images, achieved for example by scanner, Magnetic Resonance Imaging or angiography.

Apart from its production time, the manual stitching of a synthetic endoprosthesis wall has an additional disadvantage: manual sutures are put in around and near the windows or branches. Zones of less watertightness and weaker mechanical performance are created in the region of these sutures.

There is therefore a risk of blood leaks from the wall of the prosthesis, in unexpected locations. The performance of current endoprostheses can therefore be improved.

Also, the anatomical features of the walls of the natural cavity to be treated, such as unusual angulation or the presence of calcifications, cannot be taken into account optimally when the prosthesis is made manually.

To accelerate the design and production process of endoprostheses, to reduce the risks of malfunction due to mechanical sutures, to better adapt to difficult anatomies, and to improve the quality of these prostheses, it has been proposed to produce a mandrel forming a mould in the image of the natural cavity of the patient. The endoprosthesis, optionally windowed or branched, is made from this mandrel. Patent application US 2013/0296998 describes such a production process during which boreholes are made to create the windows and the branches of the final prosthesis.

The windows and the branches are positioned on the mandrel so they correspond best to the anatomy of the patient. They can be completed after demoulding of the mandrel on another mandrel corresponding to each branch.

DISCLOSURE OF THE INVENTION

As a result, there is a need for a production method of made-to-measure windowed endoprostheses corresponding to the anatomy of a natural cavity, which is automated, fast and more adapted to the precise anatomy of the lesion being treated. The cost can also be optimised relative to a prosthesis with many manual sutures.

The process shall expedite the production of endoprostheses in series from three dimensional images of patients and the obtaining of high-quality prostheses and having improved mechanical properties.

There is an additional need for a production method of a windowed or branched endoprosthesis of covered type including a synthetic wall, with or without metallic mesh. The reinforcements in the region of the windows and/or the metallic mesh shall exhibit good cohesion with the prosthetic wall in the superposition zones with this wall.

In this regard, according to a first aspect, the invention relates to a method for producing a vascular endoprosthesis intended to be inserted into a natural cavity of an individual from a three-dimensional model of the natural cavity, said model comprising a main channel and at least one branch extending from the main channel, the process comprising steps of:

obtaining an imprint structure designed to follow a shape of the main channel, the imprint structure comprising at least one location in correspondence with the intersection of the three-dimensional model, producing a prosthesis wall by means of the imprint structure, the prosthesis wall being made of polymer, a prosthesis window or a prosthesis branch being made in the region of the location, obtaining of the vascular endoprosthesis comprising the prosthesis window or the prosthesis branch.

According to this method, production of a covered prosthesis (comprising a wall made of polymer) comprises obtaining an imprint structure which takes into consideration the anatomical positioning of the different aortic branches.

A windowed or branched endoprosthesis comprising a prosthesis window or a prosthesis branch is produced from this imprint structure, in which a location of branch or window identifies an intersection between a main channel and a channel branch.

The resulting prosthesis can then be implanted in a patient and its positioning within the natural cavity of the patient can be controlled during implantation (typically by means of a drop system). The initial implantation position can be selected so that, after expansion of the prosthesis, windows or branches of the prosthesis are superposed at the intersections between the main channel and the vascular branches.

An advantage of the process is obtaining a bespoke vascular endoprosthesis in automated mode and quickly.

Costs and production times are very limited, especially as acquisition of the prosthesis model and production of the prosthesis need minimal human intervention.

The design and production time of the windowed endoprosthesis can consequently be reduced from obtaining the medical images.

In the event where the vascular endoprosthesis also comprises a metallic mesh and/or one or more reinforcements in the region of the intersections, the metallic mesh and/or the reinforcement(s) can also be made secure with the wall made of polymer, without stitching during production of the wall.

The production method of the invention can also comprise the following additional and nonlimiting characteristics, taken singly or in any one of their technically possible combinations:

the process comprises a step for placing a reinforcement on the location of the imprint structure, prior to production of the prosthesis wall, the prosthesis window or the prosthesis branch being made on the reinforcement.

In this last variant, a first advantage is avoiding putting in manual sutures to secure the reinforcements of the prosthesis with the wall made of polymer.

This avoids creating zones of mechanical weakness in the final endoprosthesis after expansion, conducive to any ruptures or fluid leaks.

The reinforcements of the prosthesis are placed with preferably at least millimetre precision in the region of the intersections between the vascular main channel and the vascular branches.

A second advantage of this variant is improving the anatomical match between the windows or branches of the resulting prosthesis even further on completion of the process and the intersections between the real main channel and the real branches of the natural cavity;

the imprint structure is obtained by 3D printing, for example by deposit of molten material or FDM;
the imprint structure is full and the prosthesis wall is made by moulding above the imprint structure;
the method comprises an intermediate location step along the imprint structure of a metallic mesh intended to extend along at least part of the vascular endoprosthesis, the prosthesis wall being made around the metallic mesh;
said location of the imprint structure comprises a cylindrical volume forming a protrusion, the location of the reinforcement comprising positioning of the reinforcement against the protrusion.

An associated technical advantage is to make the positioning of the reinforcement easier and more precise, for example of the lug, in correspondence with the intersection of the three-dimensional model;

the production of the prosthesis wall comprises winding of filaments of polymer around the imprint structure and/or coating of the imprint structure by layers of polymer;
the imprint structure is driven in rotation during production of the prosthesis wall;
the reinforcement comprises a lug, preferably made at least partially of nitinol;
sensors are placed against the imprint structure prior to production of the prosthesis wall;
the prosthesis wall is composed for the most part of polytetrafluoroethylene called PTFE or polyethylene terephthalate called PETE;
the reinforcement is composed for the most part of nitinol;
the process comprises a supplementary step for production of a branch wall by means of a branch imprint, the branch wall being made of polymer, the branch imprint being placed in the region of the location during production of the branch wall,
the resulting vascular endoprosthesis comprising the branch wall connected to the prosthesis wall;
the three-dimensional model of the natural cavity comprises discontinuity of the main channel, such as tortuosity, calcification or thrombus.

According to a second aspect, the invention relates to a vascular endoprosthesis, for example an aortic endoprosthesis, comprising a window and/or a branch, the endoprosthesis being obtained by a production method such as defined hereinabove.

According to a third aspect, the invention relates to a production apparatus for producing a vascular endoprosthesis, the apparatus being configured to carry out a production process such as defined hereinabove, the apparatus comprising:

a unit for obtaining an imprint structure by 3D printing;
a production unit of a prosthesis wall from the imprint structure;
a processing unit configured to control production of the imprint structure by the production unit as a function of a three-dimensional model of a natural cavity, the processing unit comprising a memory to save the three-dimensional model.

The endoprosthesis production apparatus according to the invention can function in automated mode with a very minimal intervention by the operator. In fact, the three-dimensional model is used to create an imprint structure, then to produce a windowed or branched endoprosthesis adapted to the morphology of the cavity.

Also, such an apparatus attains a speed greater than that of systems of the prior art since production of the prosthesis wall can be performed directly on the imprint structure without the need for drilling or manual stitching.

Optionally and nonlimiting, the endoprosthesis production apparatus also comprises a model acquisition unit configured to acquire images of a natural cavity of a patient and to generate a three-dimensional model of the natural cavity from said images.

This endoprosthesis production apparatus optionally and nonlimiting comprises a model acquisition unit configured to acquire images of a natural cavity of a patient and generate a three-dimensional model of the natural cavity from said images.

BRIEF DESCRIPTION OF THE FIGURES

Other characteristics, aims and advantages of the invention will emerge from the following description which is purely illustrative and nonlimiting accompanied by the appended drawings, in which:

FIG. 1 is a schematic view of a production apparatus for producing a vascular endoprosthesis according to an embodiment of the invention;

FIG. 2 illustrates the steps of a production process of an endoprosthesis according to an embodiment;

FIG. 3 is a schematic view of a three-dimensional model of an aorta generated by computer, comprising annotations;

FIG. 4 is a view of an imprint structure according to a first variant, made in accordance with the model of FIG. 3;

FIG. 5 is a view of an imprint structure according to a second variant.

FIG. 6 illustrates the imprint structure of FIG. 4 after placing reinforcements and a metallic mesh;

FIG. 7 is a view in perspective of a covered windowed prosthesis prior to expansion, obtained on completion of the production process;

FIG. 8 illustrates the endoprosthesis of FIG. 7, after expansion in the aorta;

FIG. 9 is a view of an imprint structure according to a third variant.

DETAILED DESCRIPTION

A production process of an endoprosthesis comprising an external wall is described hereinbelow, the endoprosthesis being intended to extend along a main channel of a natural cavity, as well as perforations in the region of branches of the natural cavity extending from the main channel.

The natural cavity is a cavity of a human or animal patient.

Such a prosthesis constitutes an expandable implantable medical device (or IMD), which can adopt an end position within a natural cavity which is different to its initial position (prior to deployment), and which is also different to its rest position.

The external wall and the perforations of the prosthesis are designed so as not to obstruct the intersection between the main channel and the branches, after expansion of the prosthesis.

It is evident that the advantages of the invention, relating to use of an imprint structure reproducing the vascular lumen, apply in the same way for a prosthesis comprising one or more windows (windowed prosthesis) and/or comprising one or more branches (branched prosthesis). "Prosthesis branch" means a wall extending along a branch of the natural cavity, said wall being connected to the prosthesis wall extending along the main channel of the natural cavity.

A prosthesis designed for a natural cavity which is not to include a branch can also be designed by means of the imprint structure of the invention.

The word "prosthesis" relates to a vascular endoprosthesis (precisely aortic) hereinbelow. In addition, throughout the following similar elements will be designated by the same references numerals in the description and in the attached figures.

Production Apparatus for Producing a Vascular Endoprosthesis

FIG. 1 illustrates a production apparatus of a prosthesis according to an embodiment of the invention.

Said apparatus can be installed in a site for series production of prostheses, in a hospital, medical laboratory, enterprise, etc. It comprises a unit 51 for obtaining an imprint structure and a unit 53 for moulding and demoulding a prosthesis membrane, controlled by a processing unit 52.

The unit 51 is configured to produce an imprint structure on command, and from a three-dimensional model generated by computer. "Imprint structure" means a support, full or hollow, against which a membrane and/or a metallic mesh can be made, moulded for example, to take the preferred form of the prosthesis prior to expansion. The imprint structure constitutes a reproduction of the vascular lumen of the natural cavity to be treated.

Highly advantageously, the unit 51 is configured to produce imprint structures by 3D printing.

Advantages of 3D printing are its quick execution, its character widely used in the materials field, and its precision.

As an alternative, the unit 51 for obtaining imprint structures can be configured to adapt already existing imprint structures to the natural cavities of patients, for example by cutting. It is possible to reuse a single imprint structure several times. The aim is still to make the made-to-measure prosthesis. The resulting prosthesis by the production process described hereinbelow is therefore preferably for one-off use.

The unit 52 is configured to carry out production (typically moulding then demoulding) of a synthetic prosthesis from an imprint structure on command, according to the modalities which will be described hereinbelow.

The processing unit 53 is configured to control the unit 51 and the unit 52. In this way, the unit 53 preferably comprises a processor on which instructions for transferring instructions to the units 51 and 52 are programmed from code.

In particular, the unit 51 is configured to receive instructions for performing 3D printing of imprint structures from the processing unit 52.

As an alternative, two separate processing units can control the operations of units 51 and 52.

For communication of instructions and computer data, an electronic link is set up between the processing unit 53 and each of the units 51 and 52, according to any type of wired or wireless link.

Preferably, the processing unit 53 is also configured to communicate with an acquisition unit 55 of a three-dimensional model of the natural cavities of a patient.

The unit 55 is configured to acquire views for reconstituting a three-dimensional image of a region of interest by X-ray imaging, by angiography or by any other medical imaging technique adapted to the natural cavity to be treated.

As an alternative, the views for reconstituting the three-dimensional model can originate from a remote database, here noted 54.

A display device 56 connected to the processing unit 53 and/or to other elements of the apparatus of FIG. 1 comprising a graphical interface can also be provided.

Production Process of a Vascular Endoprosthesis

FIG. 2 illustrates the steps of a production process of a windowed prosthesis according to an embodiment of the invention.

The apparatus described hereinabove in relation to FIG. 1 is capable of carrying out this process.

At an optional step 100, medical images of a natural cavity to be treated are acquired and registered by the acquisition unit 55. The images are acquired for example by angiography or by X-rays.

Hereinbelow, the natural cavity to be treated will be an aorta of an individual. The context here is the aortic assembly, from the ascending aorta and the arch in the region of its different branches, but also in the following portions of the aorta in the region of the thoraco-abdominal branches. These aortic branches can also be produced for other particular anatomical conformations: surgical prosthetic installations, aortic dissections, etc.

As an alternative to continue the prosthesis production process, medical images already available, for example registered in a remote database, can be used.

The images can be two-dimensional or three-dimensional.

At a step 200 a three-dimensional model of a natural cavity of a patient is generated from views of the natural cavity to be treated. The three-dimensional model is constituted for example by three-dimensional apices placed in a virtual marker (X, Y, Z). The model can also comprise surface elements joining said apices. The surface formed by the surface elements corresponds to the surface of the walls of the natural cavity.

FIG. 3 illustrates an example of a three-dimensional model 10. The aorta comprises a main channel 11 and a plurality of channel branches extending from the main channel. Two of said branches have the reference 12 in the figure. The aorta also comprises two iliac arteries 14 which extend the main channel 11 downwards.

It is noted here that the three-dimensional model 10 was obtained from views of an aorta of an individual presenting an aneurism. The aneurism extends for example from the iliac arteries 14 as far as the zone of the abdominal aorta located above the branches 12.

Zones 13 which correspond to intersections between the main channel 11 of the abdominal aorta and the aortic branches 12 are also shown on the model of FIG. 2. So as not to block the passage of blood in the aortic branches 12, the windows of the prosthesis must be aligned with the intersections 13 after expansion of the prosthesis.

To treat the aneurism, the aim is to make a windowed prosthesis of which a synthetic wall will create, after implantation and expansion of the prosthesis, a passage for blood of which a cross-section is more reduced than the cross-section of the aneurism.

By way of advantage, the acquisition unit of the three-dimensional model can also be configured to detect a central line L of the three-dimensional model of the natural cavity, along which the windowed prosthesis is intended to extend after implantation.

As an alternative, instead of generating a model of the natural cavity during production of the prosthesis, a model acquired previously can be used, or a generic model can even be used.

At a step 300, an imprint structure is obtained from a three-dimensional model of the natural cavity. The imprint structure enables production of a prosthesis wall. Advantageously, the imprint structure is a moulding mandrel.

The imprint structure matches the vascular lumen, here the aortic lumen. "Matches" means that a wall of the imprint structure, corresponding to the zone on which a wall of the prosthesis will later be moulded, follows a form of the internal wall of the aortic lumen.

Preferably, a new imprint structure is made from zero after the three-dimensional model has been obtained.

In an embodiment, the imprint structure is full. A volume of the imprint structure corresponds to an internal volume of the vascular lumen. The imprint structure accordingly has a general shape constituted by one or more tubes.

In the following example, the structure is a full mandrel 20.

FIG. 4 illustrates a mandrel 20 according to the three-dimensional model of FIG. 3.

This mandrel is constituted by a first tubular volume 21 corresponding to the abdominal aorta, and two tubular volumes 24 corresponding to the iliac arteries.

The anatomical features of the natural cavity to be treated (for example calcifications, tortuosity, thrombus, aneurisms) are taken into account for obtaining the mandrel.

The mandrel comprises specific locations which correspond to the intersections 13 of the three-dimensional model between the main channel and the branches.

During subsequent moulding of the prosthesis wall from a mandrel 20, each of said locations forms a window or a prosthesis branch on the zone provided for passage of vessels of the natural cavity after expansion of the prosthesis.

Here, the locations corresponding to the branches 12 of the model are protrusions 23*a*. The protrusions 23*a* are cylindrical volumes of minimal length, extending from the wall of the volume 21 of the mandrel.

As an alternative, the locations corresponding to the intersections 13 are perforations.

Highly advantageously, the imprint structure (here the mandrel) is obtained by 3D printing.

Apart from its speed, 3D printing has the advantage of very precisely matching the three-dimensional model of a natural cavity obtained earlier. Also, 3D printing is very easy to automate.

The mandrel 20 is made for example of polymer or metal.

For ease of subsequent demoulding of the mandrel, the mandrel can be constituted by several volumes which can be separated easily at the ends. For example, these volumes are adhered or attached together during moulding and can then be separated.

According to an alternative mode the moulding imprint structure can be not full, but hollow. The imprint structure is therefore a hollow mould. The prosthesis wall in this case will be made against an internal wall of the mould.

FIG. 5 illustrates a mould according to this alternative mode. The mould comprises a mould part 21 corresponding to the abdominal aorta, as well as mould parts 24 in the extension of the part 21, the parts 24 corresponding to the iliac arteries.

To obtain locations intended for positioning of the reinforcements and moulding of the windows, mouths 23*b* can be presented in the internal wall of the mould.

As a variant, to obtain the imprint structure matching the three-dimensional model, an already existing imprint structure is used as starting point, for example a mandrel. To ensure that the mandrel corresponds to the natural cavity to be treated, deformations or cutouts of the mandrel can be made.

In reference again to FIG. 2, the production process of the windowed prosthesis comprises an optional step 400 for positioning at least one reinforcement in the region of a location of the imprint structure.

As pointed out hereinabove, the locations of the imprint structure form windows or branches of the prosthesis for passage of blood in the aortic branches. By way of advantage, reinforcements are positioned against a wall of the imprint structure to ensure watertightness of the zones enclosing the windows or the branches of the final prosthesis.

FIG. 6 illustrates the mandrel 20 after positioning of several reinforcements at step 400.

Here, the reinforcements are lugs 33 placed against the protrusions which correspond to the intersections between the main channel and the aortic branches. In particular, lugs are placed around the two protrusions 23*a*.

The lugs here are rings of minimal thickness, preferably a thickness of less than the length of the protrusions. A material for the lugs is preferably a biocompatible metal such as nitinol or else polymer.

Optionally and advantageously, at a step 450 wires 32 of expandable metallic mesh are also placed around the mandrel. This metallic mesh is constituted by nitinol for example, or alternatively by another biocompatible alloy.

For example, a metal stent made previously and tubular in shape is placed around the mandrel. Several metal stents can be put end-to-end if necessary (especially in the example of FIG. 7, wherein the low end of the mandrel comprises two legs which correspond to the two iliac arteries).

This metallic mesh 32 is intended to extend along at least part of the vascular windowed endoprosthesis, as will be seen hereinbelow. The mesh could be placed on the mandrel prior to the reinforcements 33.

This metallic mesh is advantageous for obtaining a stiffer prosthesis which has better mechanical performance. Zones of watertightness result in the zones where the calibre of the aorta is normal compared to the pathological area.

Optionally, sensors 42 are placed on the mandrel. These sensors are intended to be incorporated into the prosthetic wall and operate during the lifecycle of the prosthesis.

In reference again to FIG. 2, the production process of the windowed prosthesis continues with production of the synthetic wall of the prosthesis at step 500.

The production is here made by moulding from the imprint structure, here from a mandrel 20.

By way of advantage, the prosthetic wall is made of polymer. The selected polymer preferably enables expansion of the prosthesis after its implantation in a natural cavity.

The prosthesis moulded in this way constitutes an expandable wall of the windowed endoprosthesis, forming a blood vessel. Here, the natural cavity is affected by an aneurism; the produced prosthesis comprises a wall of lesser cross-section than the cross-section of the aneurism.

In the event where the final prosthesis must include a metallic mesh along at least part of its length, the prosthetic wall is made around the metallic mesh so as to incorporate the wires of this mesh.

Here, since the mandrel is full, the prosthetic wall is made above the mandrel and around the reinforcements 32 and the wires 33 of metallic mesh.

If the imprint structure is hollow (as in FIG. 5), the wall can be moulded inside the imprint structure by classic moulding techniques so that the wall matches the internal wall of the mould.

Several techniques are possible for production of the prosthesis wall at step 500:

Winding or coating of the mandrel by layers and/or filaments of synthetic materials (for example polytetrafluoroethylene, called PTFE) around the mandrel, and casting of a matrix made of polymer incorporating the filaments and also incorporating the reinforcements and the wires of metallic mesh.

During winding and/or coating, according to a variant possible of the production process the imprint structure is driven in rotation, for example about a longitudinal axis of the imprint structure;

Deformation of a preexisting tube made of polymer to match the walls of the mandrel, by incorporating the window reinforcements and the wires of metallic mesh in the tube made of polymer;

Projection of polymers onto the mandrel in several layers by incorporating wires of metallic mesh or the entire metallic reinforcement structure;

Use of a backing mould press to apply the layers of polymer applied to the mandrel;

Combination of these different techniques.

To carry out the moulding, the polymer material constituting the wall 31 is brought to a sufficiently high temperature to be deformable.

A polymer material advantageous for moulding of the prosthesis is polytetrafluoroethylene, also called PTFE. Polyethylene terephthalate, called PETE, can also be used.

Hereinbelow, the prosthesis is demoulded at a step 600.

If the imprint structure is a full mandrel, demoulding comprises removal of the mandrel without damaging the prosthesis wall enclosing it.

If the imprint structure is a hollow mould, the mould is simply removed once the prosthesis has stiffened.

FIG. 7 illustrates an example of a resulting windowed vascular endoprosthesis after moulding and demoulding, from the mandrel of FIG. 6.

Here, the windowed endoprosthesis 30-1 is visible prior to expansion. This is the state of rest of the prosthesis, prior to its implantation. In this state, the prosthesis is not stressed mechanically.

The prosthesis accordingly comprises a wall 31 made of polymer. The reinforcements 33, the wires 32 of the mesh and the sensors 42 are incorporated into the wall.

Thus, it is unnecessary for the prosthesis to comprise sutures for stitching the metallic parts.

Also, the prosthesis terminates downwards via two passages 36 corresponding to the iliac arteries.

Advantageously, it is noted that a radial extension of the imprint structure 20 and consequently a resulting radial extension of the wall 31 made of polymer are both greater than a radial extension of the main channel 11 of the three-dimensional model 10 of the natural cavity to be treated.

A "radial extension" of the main channel 11 of the three-dimensional model 10 is identified relative to the central line L (illustrated in FIG. 3) of the main channel 11. On a cross-sectional plane given transversally to the central line L the radial extension of the main channel 11 is equal to the maximal distance between two points of the main channel 11 located in said cross-section plane.

A "radial extension" of the imprint structure 20 and a "radial extension" of the wall 31 of the resulting prosthesis 30-1 are both identified similarly relative to a longitudinal curve. The longitudinal curve of the imprint structure 20 is the image of the central line L. The longitudinal curve of the wall 31 is also the image of the central line L.

Preferably, the radial extension of the imprint structure 20 is between 101% and 130% of the radial extension of the main channel 11 of the natural cavity, even more preferably between 110% and 120% of the radial extension of the main channel 11 of the natural cavity.

In other words, the resulting prosthesis 30-1 is slightly oversized compared to the three-dimensional model 10. This can also be "oversizing" of the prosthesis 30-1.

An associated advantage is to promote better fixing of the resulting prosthesis 30-1 against the walls of the natural cavity, after implantation of the prosthesis 30-1. This is how the watertightness of the resulting prosthesis is reinforced with respect to flow of biological fluids such as blood within the natural cavity.

FIG. 8 illustrates the same windowed endoprosthesis in a state 30-2 after expansion in the aorta 1 of a patient.

The aorta 1 comprises the main channel 2 and the branches 3.

After its implantation via an implantation device (for example a catheter), the prosthesis undergoes mechanical stresses exerted by the surrounding walls of the cavity.

Under the effect of these stresses, the prosthesis can be compressed, causing localised decrease in its cross-section and localised extension.

An extension length 34 of the wall 31 and an extension length 35 of the metallic mesh beyond the edges of the wall 31 are illustrated, after expansion of the prosthesis in the aorta. The wall here extends over around 90% of the total length of the prosthesis after expansion.

A bespoke vascular endoprosthesis has been made, highly faithful to the anatomy of the natural cavity to be treated and the mechanical properties of which (watertightness, mechanical performance) are improved.

FIG. 9 illustrates an alternative example of imprint structure 20' for obtaining a prosthesis wall.

The imprint structure 20' is a full mandrel on which a prosthesis wall can be made by moulding, with a plurality of prosthesis branches.

The imprint structure 20' comprises a bent tube 21 corresponding to the main channel of the aortic arch.

It also comprises three imprints 23c corresponding to three branches of the aortic arch.

Metallic wires of a metallic mesh 32 are arranged on the tube 21' and on the imprints 23c.

In this example, the imprints 23c extend over a greater length relative to a length of the tube 21, compared to the protrusions 23a of the imprint structure of FIG. 4. In particular, the imprint 23c located to the right of the figure has a longitudinal extension greater than 10% of the longitudinal extension of the tube 21 along the central line.

The invention claimed is:

1. A method for producing a vascular endoprosthesis intended to be inserted into a natural cavity of an individual from a three-dimensional model of the natural cavity, said model comprising a main channel, at least one channel branch extending from the main channel, and an intersection between the main channel and the channel branch,
the process comprising steps of:
   obtaining an imprint structure designed to follow a shape of the main channel,
   the imprint structure comprising at least one location in correspondence with the intersection of the three-dimensional model,
   placing a lug on said location of the imprint structure,
   moulding a prosthesis wall above the imprint structure, the prosthesis wall being made of polymer, a prosthesis window or a prosthesis branch being made in the region of said location of the imprint structure,
   demoulding the prosthesis wall from the imprint structure, thereby obtaining the vascular endoprosthesis comprising the prosthesis window or the prosthesis branch.

2. The method for producing an endoprosthesis according to claim 1, wherein the imprint structure is obtained by 3D printing.

3. The method for producing an endoprosthesis according to claim 1, wherein the main channel includes a central line, and wherein a radial extension of the imprint structure relative to a longitudinal curve image of the central line is between 101% and 130% of a radial extension of the main channel relative to the central line.

4. The method for producing an endoprosthesis according to claim 1, wherein said location of the imprint structure comprises a cylindrical volume forming a protrusion, the location of the reinforcement comprising positioning the reinforcement against the protrusion.

5. The method for producing an endoprosthesis according to claim 1, wherein the production of the prosthesis wall comprises winding of filaments of polymer around the imprint structure, and/or coating of the imprint structure by layers of polymer.

6. The method for producing an endoprosthesis according to claim 1, comprising an intermediate step of placing, along the imprint structure, a metallic mesh intended to extend along at least part of the vascular endoprosthesis, the prosthesis wall being made around the metallic mesh.

7. The method for producing an endoprosthesis according to claim 1, wherein the lug is made at least partially of nitinol.

8. The method for producing an endoprosthesis according to claim 1, further comprising driving the imprint structure in rotation during production of the prosthesis wall.

9. The method for producing an endoprosthesis according to claim 1, further comprising placing sensors against the imprint structure prior to production of the prosthesis wall.

10. The method for producing an endoprosthesis according to claim 1, wherein the prosthesis wall is composed for the most part of polytetrafluoroethylene called PTFE or polyethylene terephthalate called PETE, and/or wherein the lug is composed for the most part of nitinol.

11. The method for producing an endoprosthesis according to claim 1, further comprising:
   placing a branch imprint in the region of the location;
   moulding a branch wall above the branch imprint, the branch wall being made of polymer, wherein the resulting vascular endoprosthesis comprises the branch wall connected to the prosthesis wall.

12. The method for producing an endoprosthesis according to claim 1, wherein the three-dimensional model of the natural cavity comprises a discontinuity of the main channel such as tortuosity, calcification or thrombus.

13. A method for producing a vascular endoprosthesis intended to be inserted into a natural cavity of an individual from a three-dimensional model of the natural cavity, said model comprising a main channel, at least one channel branch extending from the main channel, and an intersection between the main channel and the channel branch,
the process comprising steps of:
   obtaining a hollow imprint structure designed to follow a shape of the main channel,
   the imprint structure comprising at least one location in correspondence with the intersection of the three-dimensional model,
   placing a lug on said location of the imprint structure,
   moulding a prosthesis wall inside the imprint structure, the prosthesis wall being made of polymer, a prosthesis window or a prosthesis branch being made in the region of said location of the imprint structure,
   demoulding the prosthesis wall from the imprint structure, thereby obtaining the vascular endoprosthesis comprising the prosthesis window or the prosthesis branch.

* * * * *